United States Patent [19]

Yamashita et al.

[11] Patent Number: 4,895,947

[45] Date of Patent: Jan. 23, 1990

[54] PROCESS FOR PRODUCING 1-ACYL-2-PYRAZOLINE DERIVATIVE

[75] Inventors: Hiroyuki Yamashita, Fukuoka; Kunio Okumura, Kanagawa; Hajime Iizuka, Kanagawa; Norio Ohto, Kanagawa, all of Japan

[73] Assignee: Mitsui Toatsu Chemicals, Inc., Tokyo, Japan

[21] Appl. No.: 281,748

[22] Filed: Dec. 9, 1988

[30] Foreign Application Priority Data

Dec. 17, 1987 [JP] Japan ................. 62-317446

[51] Int. Cl.$^4$ ............... C07D 403/12; C07D 401/12; C07D 231/06
[52] U.S. Cl. ............................ 544/405; 544/406; 546/256; 546/279; 548/379
[58] Field of Search ............ 548/379; 544/405; 546/279, 256

[56] References Cited

U.S. PATENT DOCUMENTS

| | | | |
|---|---|---|---|
| 3,666,772 | 5/1972 | Stapfer et al. | 548/379 |
| 3,952,010 | 4/1976 | Garber et al. | 548/379 |
| 4,250,185 | 2/1981 | Gaughan | 548/379 |
| 4,839,376 | 6/1989 | Yamashita et al. | 548/379 |

OTHER PUBLICATIONS

Stapfer et al., J. Het. Chem., vol. 7, pp. 651–653, (1970).
Curtius et al., Ber. 27, 770 (1894).
J. Chem. Soc., 468 (1952), S. G. Beech et al, "Alicyclic Compounds. Part I. The Formation of Cyclopropanes in the Kishner–Wolff Reduction of $\alpha\beta$...".

Primary Examiner—Mukund J. Shah
Assistant Examiner—Cecilia Shen
Attorney, Agent, or Firm—Nixon & Vanderhye

[57] ABSTRACT

1-Acyl-2-pyrazoline derivatives represented by the formula

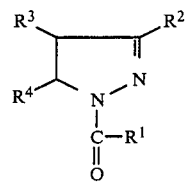

where $R^1$ denotes a hydrogen atom, pyridyl group, pyrazinyl group, alkyl group, aryl group, or alkoxy group; and $R^2$, $R^3$, and $R^4$ independently denote a hydrogen atom, furyl group, pyridyl group, alkyl group, or aryl group, are produced by cyclizing by heating an acylhydrazone derivative represented by the formula

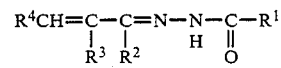

where $R^1$, $R^2$, $R^3$, and $R^4$ are defined as above, to produce compounds having useful anti-cerebral edema activity.

16 Claims, No Drawings

PROCESS FOR PRODUCING 1-ACYL-2-PYRAZOLINE DERIVATIVE

The present invention relates to a new process for producing a 1-acyl-2-pyrazoline derivative.

1-Acyl-2-pyrazoline derivatives have anticerebral edema activity and are compounds useful as drugs and as intermediates thereof.

BACKGROUND OF THE INVENTION

A 2-pyrazoline derivative having an acyl group at position 1 can be prepared by reacting a 2-pyrazoline derivative with an acid chloride or acid anhydride.

The present inventors have described certain 1-acyl-2-pyrazoline derivatives having anti-cerebral edema activity as disclosed in our copending application Ser. No. 206,812 filed on June 15, 1988, now U.S. Pat. No. 4,839,376 the disclosure of which is hereby incorporated by reference, and synthesized such derivatives according to the above-mentioned process.

This process, however, has a disadvantage in that the 2-pyrazoline derivative as the starting material is unstable and difficult to synthesize. For example, if 5-phenyl-2-pyrazoline is to be synthesized by the reaction of cinnamaldehyde with hydrazine, it is necessary to use a large excess of hydrazine relative to the amount of cinnamaldehyde to prevent the formation of azine. Azine is a condensation product formed by dehydration of two molecules of cinmamaldehyde and one molecule of hydrazine. And the separation of the desired 5-phenyl-2-pyrazoline is difficult because of residual cinnamaldehyde hydrazone, which is an uncyclized compound. In addition, it is known that 5-phenyl-2-pyrazoline is isomerized into 3-phenyl-2-pyrazoline during reaction or in the presence of a base, and that it changes into 5-phenylpyrazole upon oxidation by air. (S. G. Beech et al. J. Chem. Soc., 4686 (1952))

It is an object of the present invention to provide a new process for producing a 1-acyl-2-pyrazoline derivative, which is a useful compound as mentioned above, without forming unstable intermediates and undesirable by-products.

To achieve the above-mentioned object, the present inventors found a new process for producing a 1-acyl-2-pyrazoline derivative by the heat-induced cyclization of an acylhydrazone derivative. The present invention was completed on the basis of this finding.

DETAILED DESCRIPTION OF THE INVENTION

The process of the present invention uses as the starting material an acylhydrazone derivative represented by the formula (I) below.

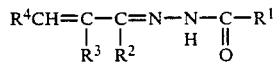
(I)

where $R^1$ denotes a hydrogen atom, pyridyl group, pyrazinyl group, alkyl group, aryl group, or alkoxy group; and $R^2$, $R^3$, and $R^4$ independently denote a hydrogen atom, furyl group, pyridyl group, alkyl group, or aryl group.

As the alkyl group, straight-chain lower alkyl groups and branched-chain lower alkyl groups are exemplified; ones with $C_1$ to 4 are preferred.

As the aryl group, an unsubstituted phenyl group and phenyl groups substituted by a lower alkyl group(s) or a halogen atom(s) are exemplified; ones with $C_1$ to 4 are preferred as said lower alkyl group(s).

As the alkoxy group, lower alkoxy groups are exemplified; ones with $C_1$ to 4 are preferred.

Examples of the acylhydrazone derivative include cinnamaldehyde hydrazone, cinnamaldehyde acetylhydrazone, cinnamaldehyde ethoxycarbonylhydrazone, cinnamaldehyde nicotinoylhydrazone, cinnamaldehyde 2-furylcarbonylhydrazone, o-methoxycinnamaldehyde nicotinoylhydrazone, crotonaldehyde nicotinolylhydrazone, crotonaldehyde pyrazinylcarbonylhydrazone, crotonaldehyde isonicotinoylhydrazone, crotonaldehyde picolinoylhydrazone, acrolein nicotinoylhydrazone, benzalacetone acetylhydrazone, 2-furylaldehyde nicotinoylhydrazone, 2-methylcinnamaldehyde nicotinoylhydrazone, benzal-2-furylmethylketone acetylhydrazone, 2-phenylcinnamaldehyde acetylhydrazone, and 2-methylaldehyde formylhydrazone.

These compounds can be readily obtained through the condensation with dehydration of an acylhydrazone represented by the formula (III) below

(III)

where $R^1$ denotes a hydrogen atom, pyridyl group, pyrazinyl group, alkyl group, aryl group, or alkoxy group, and an $\alpha,\beta$-unsaturated carbonyl compound represented by the formula (IV) below

(IV)

where $R^2$, $R^3$, and $R^4$ independently denote a hydrogen atom, furyl group, pyridyl group, alkyl group, or aryl group.

According to the process of the present invention, the desired product is produced by cyclizing the acylhydrazone derivative.

The cyclizing reaction is performed in the presence or absence of a solvent. When a solvent is used it can be an inert solvent, such as dichlorobenzene, naphthalene, biphenyl, quinoline, bibenzyl, diphenyl ether, diglyme, and nitrobenzene. The solvent can be used in any amount necessary to carry out the reaction effectively. The amount of the solvent is usually 2 to 20 times the amount of the starting material.

The reaction temperature is preferably 150° to 300° C., more preferably 200° to 250° C.

The reaction pressure is selected according to the kind of solvent used; usually the reaction pressures are in the range of atmospheric pressure to about 50 kg/cm$^2$.

The reaction may be carried out under any atmosphere; but a nitrogen atmosphere is preferable because it prevents the discoloration of the reaction liquid.

The above-mentioned reaction gives rise to a 1-acyl-2-pyrazoline derivative represented by the formula (II) below.

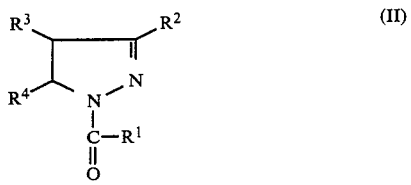

where $R^1$, $R^2$, $R^3$ and $R^4$ have the meanings as given above.

The acylhydrazone derivative of formula (I) above, wich is the starting material used in the process of the present invention, can be obtained from an acylhydrazine represented by formula (III) and an $\alpha,\beta$-unsaturated carbonyl compound represented by formula (IV), by mixing and heating them at 150° to 300° C. in an inert solvent or without using any solvent. The acylhydrazone derivative thus obtained can be made into the 1-acyl-2-pyrazoline derivative represented by formula (II) by cyclization, without being isolated from the reaction liquid.

After the above-mentioned reactions, the desired product can be isolated by recrystallization, column chromatography, or the like in the usual way.

The process of the present invention permits the synthesis of 1-acyl-2-pyrazoline derivatives having the anti-cerebral edema activity by the simple heating and cyclization of an acylhydrazone derivative, without the need of using an unstable 2-pyrazoline derivative. The process is suitable for industrial production in large quantities.

The invention will be described in more detail with reference to the following examples.

EXAMPLE 1

Synthesis of 1-benzoyl-5-phenyl-2-pyrazoline

To 200 ml of methanol solution containing 13.2 g of cinnamaldehyde was added 13.6 g of benzoylhydrazine, followed by stirring for 30 minutes at room temperature, for the precipitation of crystals. The crystals were filtered off and dried. Thus there was obtained 22 g of cinnamaldehyde benzoyl hydrazone (mp. 192°–194° C.).

Five grams of the cinnamaldehyde benzoylhydrazone was suspended in 20 ml of diphenyl ether, followed by stirring at 220° C. for 3 hours. After cooling, the reaction liquid was poured into 100 ml of hexane for the separation of insoluble matter. The insoluble matter was filtered off and recrystallized from a methanol-water solution. Thus there was obtained 3.8 g of 1-benzoyl-5-phenyl-2-pyrazoline (mp. 105°–106° C.) as the desired product. The yield was 76.0%.

EXAMPLE 2

Synthesis of 1-acetyl-5-phenyl-2-pyrazoline

To 10 ml of diphenyl ether were added 1.3 g of cinnamaldehyde and 0.8 g of acetylhydrazine, followed by gradual heating to 220° C. over 30 minutes. Stirring was continued for 3 hours at that temperature. After cooling, the reaction liquid as such was subjected to silica gel chromatography (chloroform/methanol=100/1). Thus there was obtained 1.2 g of 1-acetyl-5-phenyl-2-pyrazoline in the form of light yellowish oil as the desired product. The yield was 64.8%.

EXAMPLE 3

Synthesis of 1-nicotinoyl-5-methyl-2-pyrazoline

In 50 ml of methanol was suspended 22 g of nicotinic acid hydrazide. To the suspension was added dropwise 13.2 ml of crotonaldehyde, followed by stirring for 30 minutes at room temperature. Methanol was distilled away under reduced pressure, and the residue washed with ether, filtered off, and dried. Thus there was obtained 27.5 g of crotonaldehyde nicotinoyl hydrazone (mp. 144°–145° C.).

Nineteen grams of this hydrazone was suspended in 50 ml of biphenyl ether, followed by stirring at 200°–220° C. (bath temperature) for 3 hours. After cooling, the reaction liquid was purified by silica gel chromatography ($CHCl^3$:MeOH=100:1). Thus there was obtained 8.0 g of 1-nicotinoyl-5-methyl-2-pyrazoline in the form of an oil (bp. 143°–145° C./0.3 mmHg). The yield was 42.1%.

EXAMPLE 4

Synthesis of 1-pyrazinylcarbonyl-5-methyl-2-pyrazoline

In 50 ml of methanol was suspended 9 g of nicotinic acid hydrazide. To the suspension was added dropwise 5.4 ml of crotonaldehyde, with stirring over 30 minutes at room temperature.

Methanol was distilled away under reduced pressure, and the residue washed with ether, filtered off, and dried. Thus there was obtained 11.2 g of crotonaldehyde pyrazinylcarbonyl hydrazone (mp. 192°–194° C.).

A quantity of 3.8 g of this hydrazone was suspended in 10 ml of diphenyl ether, followed by stirring at 200°–220° C. (bath temperature) for 3 hours. After cooling, the reaction liquid was purified by silica gel column chromatography (ethyl acetate). Thus there was obtained 1.4 g of 1-pyrazinylcarbonyl-5-methyl-2-pyrazoline (mp. 77°–79° C.). The yield was 36.8%.

EXAMPLES 5 TO 12

The same procedures as in Examples 1 to 4 were repeated to give the following compounds
1-ethoxycarbonyl-5-phenyl-2-pyrazoline (yield: 67%), oily substance
1-nicotinoyl-5-phenyl-2-pyrazoline (yield: 82%), mp. 100°~102° C.
1-(2-furylcarbonyl)-5-phenyl-2-pyrazoline (yield: 51%), mp. 136°~137° C.
1-nicotinoyl-5-(2-methoxyphenyl)-2-pyrazoline (yield: 71%), mp. 93°~95° C.
1-nicotinoyl-2-pyrazoline (yield: 78%), mp. 81°~82° C.
1-acetyl-3-methyl-5-phenyl-2-pyrazoline (yield: 66%), oily substance
1-nicotinoyl-5-(2-furyl)-2-pyrazoline (yield: 48%), mp. 91°~93° C.
1-nicotinoyl-4-methyl-5-phenyl-2-pyrazoline (yield: 52%), oily substance.

What is claimed is:

1. A process for producing a 1-acyl-2-pyrazoline derivative represented by the formula (II)

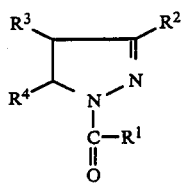

where $R^1$ denotes a hydrogen atom, pyridyl group, pyrazinyl group, alkyl group, aryl group, or alkoxy group; and $R^2$, $R^3$, and $R^4$ independently denote a hydrogen atom, furyl group, pyridyl group, alkyl group, or aryl group, said process comprising cyclizing by heating an acylhydrazone derivative represented by the formula (I)

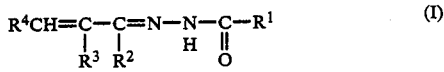

where $R^1$, $R^2$, $R^3$, and $R^4$ are defined as above.

2. The process according to claim 1, in which the cyclization is conducted at a temperature of from about 150° C. to about 300° C.

3. The process according to claim 2, in which the cyclization is conducted at a temperature of from about 200° C. to about 250° C.

4. The process according to claim 1, in which the acylhydrazone derivative is selected from the group consisting of cinnamaldehyde hydrazone, cinnamaldehyde acetylhydrazone, cinnamaldehyde ethoxycarbonylhydrazone, cinnamaldehyde nicotinoylhydrazone, cinnamaldehyde 2-furylcarbonylhydrazone, o-methoxycinnamaldehyde nicotinoylhydrazone, crotonaldehyde nicotinolhydrazone, crotonaldehyde pyrazinylcarbonylhydrazone, crotonaldehyde isonicotinoylhydrazone, crotonaldehyde picolinoylhydrazone, acrolein nicotionylhydrazone, benzalacetone acetylhydrazone, 2-furylaldehyde nicotinoylhydrazone, 2-methyl-cinnamaldehyde nicotionylhydrazone, benzal-2-furylmethylketone acetylhydrazone, 2-phenylcinnamaldehyde acetylhydrazone, and 2-methylaldehyde formylhydrazone.

5. The process according to claim 1, in which the compound prepared is 1-benzoyl-5-phenyl-2-pyrazoline.

6. The process according to claim 1, in which the compound prepared is 1-acetyl-5-phenyl-2-pyrazoline.

7. The process according to claim 1, in which the compound prepared is 1-nicotinoyl-5-methyl-2-pyrazoline.

8. The process according to claim 1, in which the compound prepared is 1-pyrazinylcarbonyl-5-methyl-5-pyrazoline.

9. The process according to claim 1, in which the compound prepared is 1-ethoxycarbonyl-5-phenyl-2-pyrazoline.

10. The process according to claim 1, in which the compound prepared is 1-nictotinoyl-5-phenyl-2-pyrazoline.

11. The process according to claim 1, in which the compound prepared is 1-(2-furylcarbonyl)-5-phenyl-2-pyrazoline.

12. The process according to claim 1, in which the compound prepared is 1-nicotinoyl-5-(2-methoxypheyl)-2-pyrazoline.

13. The process according to claim 1, in which the compound prepared is 1-nicotinoyl-2-pyrazoline.

14. The process according to claim 1, in which the compound prepared is 1-acetyl-3-methyl-5-phenyl-2-pyrazoline.

15. The proess according to claim 1, in which the compound prepared is 1-nicotinoyl-5-(2-furyl)-2-pyrazoline.

16. The process according to claim 1, in which the compound prepared is 1-nicotinoyl-4-methyl-5-phenyl-2-pyrazoline.

* * * * *